United States Patent [19]

Leitzke et al.

[11] 4,183,728

[45] Jan. 15, 1980

[54] PROCESS FOR DETERMINING THE OZONE CONTENT OF OZONE-CONTAINING GAS MIXTURES

[75] Inventors: Ortwin Leitzke, Kaarst; Josef Cremer, Hurth; Erhard Albrecht, Dusseldorf, all of Fed. Rep. of Germany

[73] Assignee: Messer Griesheim GmbH, Frankfurt am Main, Fed. Rep. of Germany

[21] Appl. No.: 876,519

[22] Filed: Feb. 9, 1978

[30] Foreign Application Priority Data

Feb. 18, 1977 [DE] Fed. Rep. of Germany ....... 2706992

[51] Int. Cl.² .................. G01N 25/20; G01N 31/06; G01N 31/10; B01D 53/04
[52] U.S. Cl. ...................... 23/232 E; 55/68; 55/75; 422/51; 422/88; 422/98; 423/239
[58] Field of Search ............ 23/232 R, 232 C, 232 E, 23/254 E, 255 E; 55/74, 75, 68; 423/239; 422/51, 83, 88, 98

[56] References Cited

U.S. PATENT DOCUMENTS

| | | | |
|---|---|---|---|
| 1,443,220 | 1/1923 | Guye et al. | 55/74 X |
| 1,992,747 | 2/1935 | Gilliland et al. | 23/232 E |
| 2,899,281 | 8/1959 | Olmer | 23/232 E X |
| 3,006,153 | 10/1961 | Cook | 55/75 X |
| 3,153,577 | 10/1964 | McCully et al. | 23/232 E X |
| 3,689,212 | 9/1972 | Petit et al. | 55/75 X |
| 3,895,094 | 7/1975 | Carter et al. | 423/239 A |

FOREIGN PATENT DOCUMENTS 2441857  3/1976  Fed. Rep. of Germany .

OTHER PUBLICATIONS

F. J. Olmer, Catalytic Atmospheric Ozone Analyzer, Ozone Chem. and Tech. Advances in Chemistry Series, Amer. Chem. Soc., pp. 87-92 (1959).

Primary Examiner—Joseph Scovronek
Attorney, Agent, or Firm—Connolly and Hutz

[57] ABSTRACT

The ozone content of ozone-containing gas mixtures is determined in a process wherein the ozone is converted to oxygen and which includes channeling a gas mixture containing nitrogen oxides and possibly water vapor through an adsorbent of aluminosilicate which contains 2 to 20% by weight of aluminum oxide and the aluminosilicate is of spherical shape with a particle diameter of 2 to 5 mm and a specific area of 200 to 650 m²/g and an average pore diameter of 5 to 10 nm.

5 Claims, 1 Drawing Figure

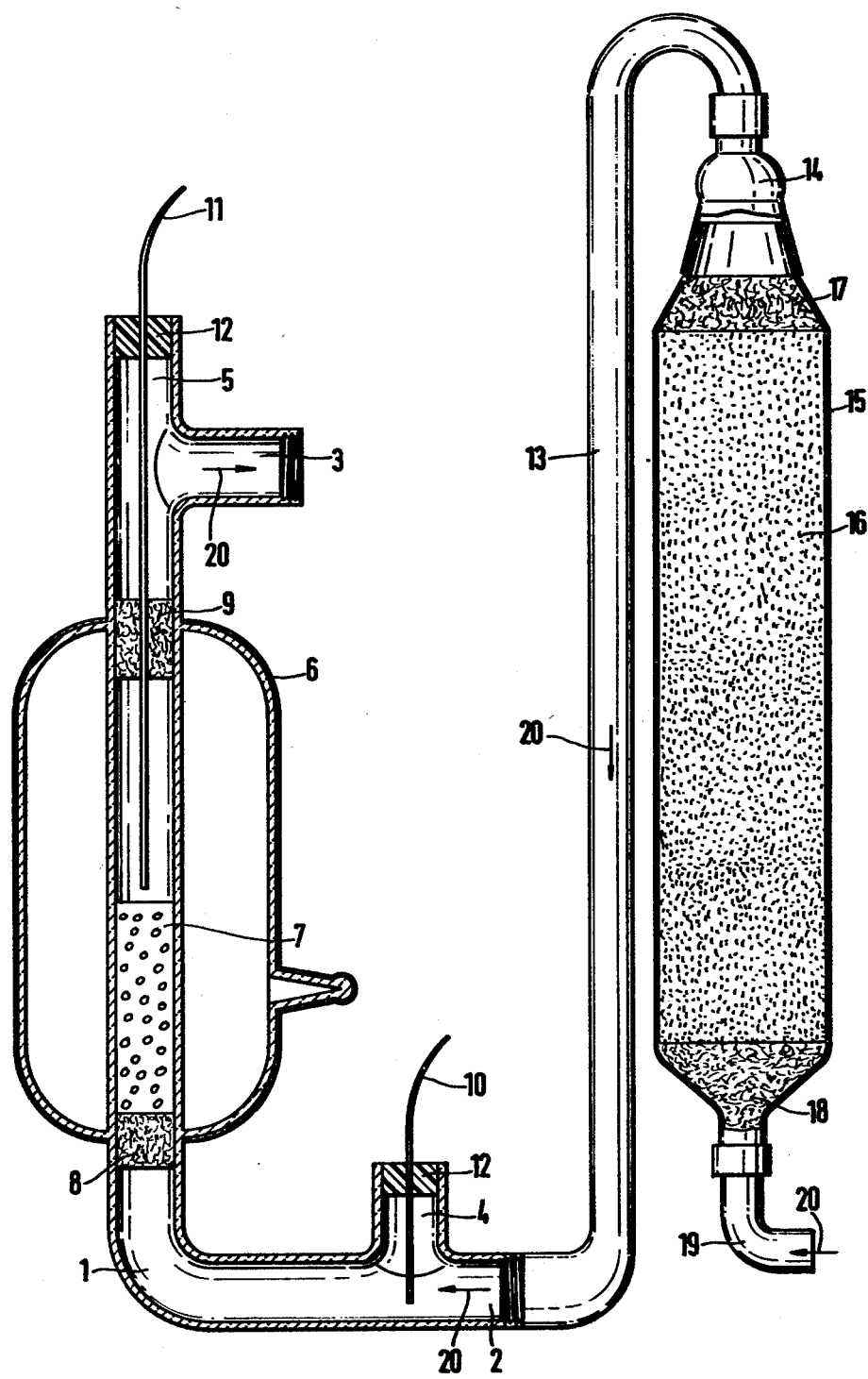

PROCESS FOR DETERMINING THE OZONE CONTENT OF OZONE-CONTAINING GAS MIXTURES

BACKGROUND OF THE INVENTION

The invention is concerned with a process and a device for determining the ozone content of ozone-containing gas mixtures according to German patent application P 24 41 857.3-52.

With the above process, the percent range of the ozone content can be continuously determined in a simple and safe manner by use of a stream of the ozone-containing gas mixture channeled over a catalyst of mixed metallic oxides (Hopcalite). The ozone is decomposed to oxygen at the catalyst with the development of heat. The temperature increase between the entering and exiting gas mixture is measured with two thermocouples which are part of a bridge circuit. The temperature difference which occurs is a measure of the ozone content of the gas mixture.

The continuous measuring of the percent range of the ozone content becomes constantly more important since the charge of ozone grows during water treatment and during the purification of exhuast gas. An accordingly simple and sure or safe measuring process was thereby made possible by the procedures described in the aforesaid German application.

With the process according to the aforesaid application, however, it turned out that the catalyst of mixed metallic oxides becomes contaminated by nitrogen oxides with prolonged use. The nitrogen oxides result, during the production of ozone, from the air, because nitrogen oxides are in part formed in the air. A similar contamination is also sometimes brought about by the available moisture.

SUMMARY OF THE INVENTION

The object of the invention is to achieve a process for ozone determination according to the aforesaid application, but with which a contamination of the catalyst by nitrogen oxides and eventually water vapor is impossible.

A process for the determination of the ozone content of gas mixtures containing ozone has been found, according to which ozone is converted to oxygen, with the production of heat, by means of a catalyst consisting essentially of a mixture of cupric oxide and manganese dioxide and the occurring temperature increase serves as a measure of the ozone concentration, in which the ozone of a stream of the gas mixture is completely converted to oxygen. The catalyst is heat insulated according to German patent application P 24 41 857.3-52 and according to this invention, in the case of gas mixtures containing nitrogen oxides and possibly water vapor, the gas mixture is channeled through an adsorbent of aluminosilicate.

It is advantageous to have the aluminosilicate adsorption medium contain 2% to 20% by weight, preferably 8% to 10% by weight, of aluminum oxide. The particle diameter of the aluminosilicate should amount to 2 to 5 mm, especially 3 to 4mm, with preferably spherical shape. The specific area of the aluminosilicate used in the invention's process amounts to preferably 200 to 650 $m^2/g$, especially preferred is 200 to 300 $m^2/g$. The range of 5 to 10 nm, especially 6 to 8 nm is best suited as the average pore diameter.

A device for carrying out the invention's process consists of: a tube with an inlet connection and an outlet connection for the gas mixture; a heat insulated catalyst located between these openings; the catalyst consists essentially of cupric oxide and manganese dioxide; and a thermocouple in each of the vicinities of the inlet connection and of the catalyst, as well as an adsorbent cell, filled with aluminosilicate, which is hooked up in exchangeable fashion before the inlet connection.

The thermocouple in the vicinity of the catalyst is most advantageously installed at the phase boundary between catalyst and gas. This has the advantage that small and also large concentrations of ozone can, with good heat insulation, be rapidly determined with little catalyst mass. The thermocouple is, to be most useful, mounted 0.1 to 10 mm, especially 0.1 to 2 mm, above the catalyst.

15 liters/hour are adequate as a partial stream in which the ozone is quantitatively determined.

Ozone contents of preferably 0.9 to 120 g ozone/$Nm^3$ can be determined according to the invention's process. Hopcalite is very suitable as catalyst. The temperature measurements are most practically done with thermocouples.

It is surprisingly that all nitrogen oxides are retained by the adsorber while the ozone, however, passes unhindered through the adsorber. The ozone determination, according to the invention, is primarily suited for such gas mixtures which consist of ozone and oxygen, ozone and air, or ozone, oxygen, nitrogen, nitrogen oxides and water vapor. The water is, like the nitrogen oxides, completely held back by the adsorber, provided that the quantity of adsorber is adequately measured out.

The advantage of the invention's process, whereby nitrogen oxides and water do not contaminate the catalyst of mixed metal oxide, is achieved because the nitrogen oxides and the water are retained by the series connected adsorber of aluminosilicate, without any decomposition of the ozone at this adsorber. This is achieved as a result of the qualitative and quantitative make-up of the aluminosilicate, its surface, and its average pore diameter. Ozone partially decomposes at room temperature on the customary silica gel, so that the quantitative determination of ozone is distorted.

The small partial stream quantity of 15 liters of gas per hour is achieved because the surface of the mixed metallic oxide catalyst at which the ozone decomposes is kept small.

Therefore, the catalyst mass consists, in practical fashion, of spheres with diameters of 0.1 to 1.2 mm, preferably 0.8 to 1.0 mm.

Small ozone concentrations of about 0.8 g ozone per $Nm^3$ of gas upwards can be measured with the invention's process. This is primarily achieved by a reduction of the heat dissipation, since the mass of the catalyst, the gas, the thermocouples and glass are kept small, together with good heat insulation.

THE DRAWING

The single FIGURE diagrammatically illustrates a device for carrying out the invention.

DETAILED DESCRIPTION

The device illustrated consists of a glass tube 1 angled 90°, which is provided with an inlet connection 2 for the ozone-oxygen mixture to be examined and an outlet connection 3. A further connection 4, through which a thermocouple 10 is introduced, is found in the vicinity of the inlet connection 2. This connection 4 is sealed by a stopper 12 of PTFE. Likewise, a further connection 5 through a thermocouple 11 is introduced, is located in the vicinity of the outlet connection 3. This connection too is sealed by a stopper 12 of PTFE. The catalyst 7, for example, of Hopcalite, is located in the glass tube 1 between the inlet connection 2 and the outlet connection 3. The catalyst 7 is held in position by the glass wool inserts 8 and 9, which allows gas to pass through. The tube 1 containing the catalyst 7 is concentrically surrounded by an additional glass tube 6. The glass tube 6 is mirrored and fused with the glass tube 1. The cavity between both tubes has a pressure of less than $10^{-5}$m bar. The catalyst 7 is therewith heat insulated. The temperature of ozone decomposition in the catalyst 7 is measured with the thermocouple 10. The temperature after ozone decomposition is measured with the thermocouple 11, which is advantageously placed on or closely above the boundary between the catalyst 7 and the gas space. The temperature difference is proportional to the ozone concentration.

At the inlet connection 2 a connecting line 13 is used, which can be made of PVC, glass or V4A steel. The free end of the connecting line 13 is connected, by means of a removable ground cap 14, with the adsorbent vessel 15, which is made of glass or V4A steel.

In the adsorber vessel 15 there is surface treated aluminosilicate as the adsorbtion medium 16 which is enclosed by the glass wool inserts 17, 18. At the other end of the adsorber vessel 15 an intake tube 19 is attached.

The direction of flow of the gas mixture is indicated by the arrow 20.

What is claimed is:
1. In a process for the determination of the ozone content of ozone-containing gas mixtures containing nitrogen oxides according to which ozone is converted to oxygen, with the production of heat, by means of a catalyst; the catalyst consists essentially of a mixture of cupric oxide and manganese dioxide, whereby the occurring temperature increase serves as a measure of the ozone concentration, whereby the ozone of a stream of the gas mixture is completely converted to oxygen, and wherein the catalyst is heat insulated; the improvement being channeling the gas mixture through an adsorbent of aluminosilicate to extract nitrogen oxide and water before measuring the ozone content, with the aluminosilicate containing 2 to 20% by weight of aluminum oxide, and the aluminosilicate being of spherical shape with a particle diameter of 2 to 5 mm and a specific area of 200 to 650 m$^2$/g and an average pore diameter of 5 to 10 mm.

2. Process according to claim 1, characterized by the fact that the aluminosilicate contains 8 to 10% by weight of aluminum oxide.

3. Process according to claim 1, characterized by the fact that the aluminosilicate has a particle diameter of 3 to 4 nm.

4. Process according to claim 1, characterized by the fact that aluminosilicate has a specific area of 200 to 300 m$^2$/g.

5. Process according to claim 1, characterized by the fact that the aluminosilicate has an average pore diameter of 6 to 8 nm.

* * * * *